Figure 1:
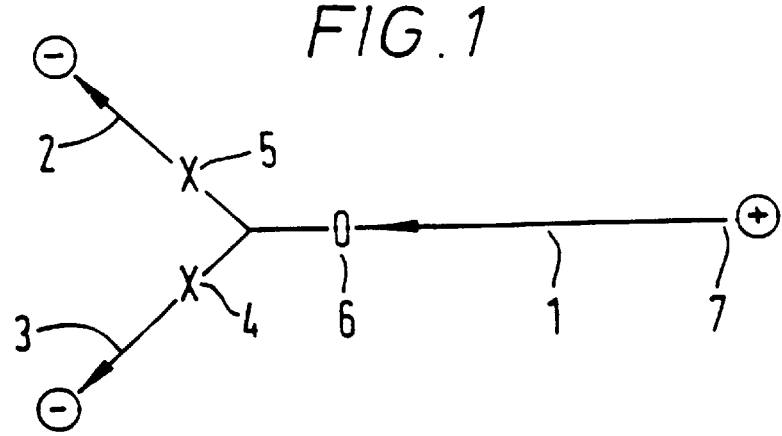

United States Patent [19]

Bevan et al.

[11] Patent Number: 6,159,744
[45] Date of Patent: *Dec. 12, 2000

[54] LIQUID FLOW MANAGEMENT MEANS

[75] Inventors: Christopher David Bevan; Ian Martin Mutton, both of Stevenage, United Kingdom

[73] Assignee: Glaxo Group Limited, Greenford, United Kingdom

[*] Notice: This patent is subject to a terminal disclaimer.

[21] Appl. No.: 09/119,935

[22] Filed: Jul. 21, 1998

Related U.S. Application Data

[63] Continuation of application No. 08/537,943, filed as application No. PCT/EP94/01790, Jun. 3, 1994, Pat. No. 5,795,788.

[30] Foreign Application Priority Data

Jun. 5, 1993 [GB] United Kingdom ............... 9311651
Jan. 29, 1994 [GB] United Kingdom ............... 9401711

[51] Int. Cl.⁷ .................................................. G01N 30/30
[52] U.S. Cl. .............................................. 436/180; 137/13
[58] Field of Search ............................ 137/13, 828, 340, 137/341, 334, 338, 606, 861, 884; 436/161, 180; 422/70, 82, 110

[56] References Cited

U.S. PATENT DOCUMENTS

| | | |
|---|---|---|
| 3,663,203 | 5/1972 | Davis et al. . |
| 4,203,472 | 5/1980 | Dulaney ................... 137/828 |
| 4,258,740 | 3/1981 | Kaartinen et al. . |
| 4,269,212 | 5/1981 | Kaartinen ................... 137/13 |
| 4,766,922 | 8/1988 | Kaartinen et al. ........... 137/13 |
| 5,014,738 | 5/1991 | Jones ........................ 137/340 |
| 5,311,896 | 5/1994 | Kaartinen .................. 137/15 |
| 5,795,788 | 8/1998 | Bevan et al. ............... 436/161 |

FOREIGN PATENT DOCUMENTS

| | | |
|---|---|---|
| 2 422 884 | 11/1979 | France . |
| WOA86 06144 | 10/1986 | WIPO . |

OTHER PUBLICATIONS

Nashabeth et al., Electrophoresis 1993 14: 407–416.

Lemmo et al., Journal of Chromatography, 663: 213–220 (1993).

Lemmo et al., Anal. Chem., 65: 1576–1581 (1993).

Manz et al., Advances in Chromatography, 33: 1–66 (1993).

*Primary Examiner*—Jeffrey Snay
*Attorney, Agent, or Firm*—Bacon & Thomas, PLLC

[57] ABSTRACT

The present invention relates to a method and apparatus for managing liquid flow through small bore tubing (1,2,3) or channels (13) by freezing the liquid or thawing the frozen liquid in a small segment of the tube or channel.

7 Claims, 1 Drawing Sheet

LIQUID FLOW MANAGEMENT MEANS

This application is a continuation application of U.S. application Ser. No. 08/537,943 filed Nov. 21, 1995, now U.S. Pat. No. 5,795,788 which is a 371 of PCT/EP94/01790 filed on Jun. 3, 1994 and which application has been allowed.

The present invention relates to an improved means for managing liquid flow in small bore tubes or channels. More particularly it relates to apparatus for managing liquid flow in microanalytical and micro-preparative procedures such as capillary electrophoresis and high performance liquid chromatography and electrochromatography.

The techniques of micro high performance liquid chromatography, electrochromatography and/or capillary electrophoresis involve the flow of a liquid phase through capillary tubing which typically has an internal diameter within the range of 2 $\mu$m to about 1000 $\mu$m e.g. 50 $\mu$m. In many of the applications of these micro- analytical and micro preparative techniques it is necessary to provide means for stopping the flow of one liquid phase in the column or tubing and introducing another liquid phase at a selected point in the capillary tubing and/or alternatively providing means for diversion of the liquid phase flow by means of additional inlets and outlets as and when required. To date such management of the flow of liquid phase through the column or tubing is achieved by means of specifically engineered switching valves with capillary tubes connected by means of sleeve connectors or unions into which the capillary tubes are located. These valves which have to be custom built to exacting specifications are very expensive and there are several operational disadvantages associated with their use. Thus the mechanical valves must be chemically inert so that the mobile phase remains uncontaminated by residues from the valve and this requirement limits the choice of the material and lubricants for the valves construction and maintenance. The fitting of the valves to the column and the construction of the additional inlets and outlets in the capillary tubing must be achieved with ideally zero dead volume couplings and unions. Further the flow through the valve should not be turbulent so that the analyte peak of interest remains narrow in order to achieve the required degree of resolution.

The problem that arises with use of sleeve connectors or unions is the generation of dead volume between the ends of each capillary. The size of the dead volume may be reduced by the careful positioning of the capillaries and ensuring clean cut ends but it is not possible to reduce the dead volume to zero or to be sufficiently small so as to be insignificant on the scale of operation of an analytical technique such as multi-dimensional electrophoresis. Thus for example simple solid geometry calculations show in a conventional Y piece sleeve connector for capillary tubing of 50 $\mu$m internal diameter and 375 $\mu$m outer diameter the minimum dead volume will be at least 23 nL and in practice it will be significantly larger. This dead volume is too large for micro-analytical techniques such as capillary electrophoresis which use injection volumes in the order of 5 nL. In these circumstances the resolution of closely spaced peaks can be compromised by convective and eddy current induced mixing which will take place in the dead volume region.

We have now found that the disadvantageous problems associated with the use of mechanical switching valves in capillary tube liquid flow systems can be avoided by the use of rapid freeze and rapid thaw of the liquid phase at appropriate segments of the capillary system. The flow of the liquid phase through the capillary tubing can be stopped if a small segment of the column is rapidly cooled so as to freeze the liquid phase in that segment. Further the thermal capacity of the small segment of the column to be frozen is very small and this allows for rapid freezing and rapid thawing as required.

The disadvantages associated with the sleeve connectors and unions can be overcome by use of micro-channel pathways to connect the various capillary tubes and the present invention provides a means for achieving this.

The present invention therefore provides a means for managing liquid flow through small bore tubing or channels which comprises a means for freezing the liquid in a small segment of the tube or channel. Preferably the means for freezing the liquid phase is a jet of cold gas directed onto the required section of the tube. Conveniently the cooling gas is provided from a liquefied source of the gas under pressure such as liquid carbon dioxide or liquid nitrogen.

Alternative means for rapidly freezing the liquid phase includes the use of a thermo electronic arrangement such as a Peltier cooling arrangement or a cold finger. A separate means such as a jet of warm air for rapidly thawing the frozen segment of the column may also be provided but this may not be necessary if the normal temperature of the environment is sufficiently high.

In a further aspect of the invention there is provided a microanalytical or micro-preparative apparatus comprising one or more inlet pathways connected to one or more outlet pathways, the pathways comprising small bore tubing or channels and means for freezing of the liquid phase in a small segment of each of the inlet or outlet pathways. Preferably said means for rapidly freezing the liquid phase is a finely directed jet of cold gas. If necessary the apparatus may also be provided with means such as a jet of warm air so as to rapidly thaw the frozen segment of the column as and when required.

Preferably the inlet and outlet pathways comprise capillary tubes. The capillary tubes may be connected by means of a rigid body in which the ends of the capillary tubes to be connected are held and micro-channels in said body providing a connection with the bores of the said capillary tubing within the rigid body. Each micro-channel connecting two capillary tubes conveniently has a cross sectional area of a similar order of magnitude to that of the internal bore of the capillary tube, but may be considerably smaller. Typically the micro-channels will have a cross sectional area of up to 2 times that of the internal bore of the capillary tube. It will be appreciated however that for a given capillary tube connecting means the shape (cross-sectional area and length) of each micro-channel may be selected on the basis of the micro-analytical procedure with which it is to be used and the physical constraints of the particular connecting means.

For use in micro-preparative procedures including micro-analytical procedures wherein it is required to prepare in situ a derivative of the analyte at least two of the micro-channels in the connecting means according to the invention, are arranged so that they form a reaction cell, or connect to or intersect at a reaction cell within the rigid body or connect with a reaction cell outside the body, for example one of the capillary tubes connected thereto.

In one embodiment of the invention the rigid body comprises a lower body member, with a flat upper surface, into which the capillary tubes to be connected are held with one end of each said capillary tube flush with the flat upper surface of the lower body member; an upper body member which has a flat lower surface; micro-channels in the flat surface of the lower and/or upper body members positioned to connect the bores of the appropriate capillary tubes; and means for securing the upper and lower body members together.

In a preferred embodiment of the invention the rigid body comprises a lower body member, with a flat upper surface, in which the capillary tubes to be connected are held with one open end of the said capillary tube flush with the flat upper surface of the body member; an upper body member which has a flat lower surface containing micro-channels such that when the lower surface is located on the upper surface of the lower body member the micro-channels therein connect the openings in the appropriate capillary tubes, and means for securing the upper and lower body members together.

In a further embodiment of the invention the rigid body comprises a lower body member, with a flat upper surface into which the capillary tubes to be connected are held with one open end of the said capillary tube flush with the flat upper surface of the body lower member, and micro-channels in the said flat upper surface connecting with the openings in each of the capillary tubes; an upper body member which has a flat lower surface which is located on the flat upper surface of the lower body member and covers the capillary tube ends and connecting micro-channels and means for securing the upper and lower body members together.

The choice of material from which the lower and upper body members are made will depend on a number of factors. Thus they must be inert to the fluids that will flow through the micro-channels and the material must be capable of being rendered to a smooth and flat surface.

The lower body member may for example be made of an epoxy or acrylic resin into which the capillary tubes are set. Alternatively the lower body member may be made of an initially solid substance such as silica and the capillary tubes may be inserted into preformed channels therein and adhesively secured in place. The capillary tubes and the body members are preferably made of silica or glass.

The upper and lower members of the body may be secured together by any convenient means. Thus for example they may be adhesively bonded or welded together. Also it may be desirable to use a suitable gasket to achieve the required sealing effect.

The freeze-thaw action provides a fast and very effective means of liquid phase flow management that is easy to operate and in particular can be automated and/or operated under remote control. Thus it can be used within packed micro-columns in situ where conventional switching valves could not operate. Further the technique may be used with any liquid phase that freezes and thus the choice of the liquid phase is not limited by factors such as the possible interaction with the mechanical valve or the lubricant therein.

When the freezing means is a jet of cold gas for liquid phases which freeze at temperatures of around $-60°$ C. or above liquid carbon dioxide is a particular suitable source of the cooling gas. For lower temperatures it may be more desirable to use liquid nitrogen.

To freeze the liquid in the desired segment of the column or micro-channel the cooled gas may be applied in any convenient manner such as from a collar around the column or micro-channel or more simply as a single jet from one side of the column. The thawing action may be achieved using a jet of warm air in a similar manner.

The cooling action to maintain the required segment of the liquid phase frozen may be applied as required throughout the time period in which the liquid phase flow is to be stopped. Thus the cooling means may be applied continuously throughout the time required to maintain the required segment in the frozen state. Alternatively the temperature of the frozen segment may be monitored and the cooling effect applied as required. The temperature of the segment to be frozen may be monitored by conventional means for example by incorporation of a suitable temperature sensor such as a liquid crystal on the outer surface of the column and means for monitoring.

The operation of each of the freeze-thaw switches may be automated and the sequence operated according to a predetermined programme. For example in procedures such as capillary electrophoresis a suitable sensor such as ultra violet detector system, or sensor electrodes may be used to monitor the analyte composition of the fluid flowing in the capillary tube or micro-channel. The freeze-thaw switching may be controlled by the response from the detector according to a predetermined programme.

When the capillary tube connecting means according to the invention is to be used in conjunction with an analytical or micro preparative procedure which involves a photolytic process then it will be appreciated that one of the capillary tubes connected thereby and the microchannel associated therewith may be used to carry the required light source.

The use of freeze-thaw switching to control the flow of the liquid phase in columns is particularly useful when applied to high performance liquid chromatography (HPLC) capillary electrophoresis (CE) in particular preparative capillary electrophoresis, multi-dimensional CE and/or HPLC-CE, combined CE or HPLC with mass spectrometry, simultaneous multi-detection schemes electrochromatography in particular capillary electrochromatography (CEC), and isotachophoresis.

Figure 2:
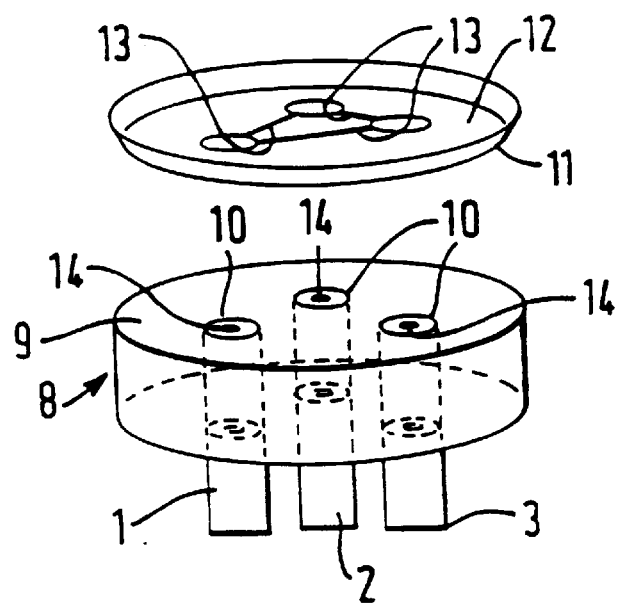
Figure 3:
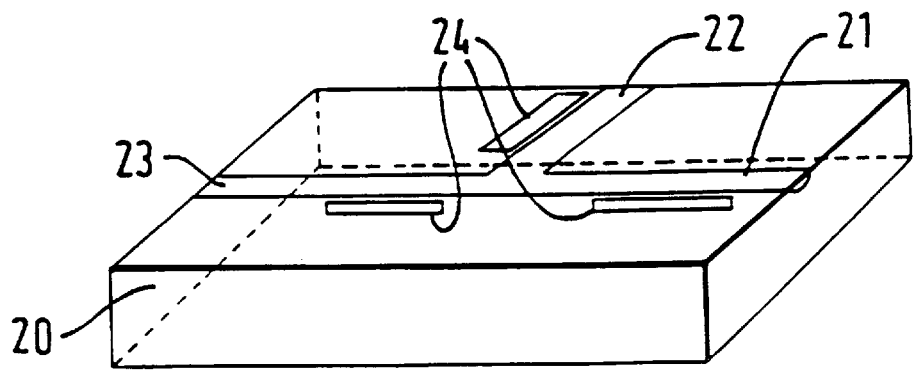

The invention is described in detail below by example only, with reference to the accompanying drawings, wherein;

FIG. 1 schematically shows the application of the freeze thaw switching procedure in the management of liquid flow in micro-preparative capillary electrophoresis;

FIG. 2 shows the capillary tube connecting means for use in apparatus for micro-analytical or micro-preparative processes according to the invention; and FIG. 3 is a detailed view illustrating a microchip with a freeze thaw switch built in.

An example of a particularly beneficial application of the freeze thaw switching procedure in the control of liquid flow is its use in preparative capillary electrophoresis and this is illustrated schematically in FIG. 1.

The apparatus consists of capillary electrophoresis column (1) which passes through an ultra-violet detector system (6) and two outlet capillary columns (2) and (3) positioned beyond the ultra violet detector. Adjacent to each of the outlet columns there are freeze-thaw switching points (4) and (5) arranged at convenient positions on each column.

The material to be separated is injected into the column (1) at the entry port (7) by repeat injections at convenient time intervals. The components of the mixture are separated by electrophoresis along column (1) and the position of each separated component is detected by the ultra-violet monitor. If the separated component is required to go into column (2) the freeze switch (4) on column (3) will be in operation to stop the liquid flow in column (3). Once the required material has passed into column (2) the freeze switch (5) will operate so as to stop the flow into column (2). At the same time the frozen fluid in column (3) will be thawed to allow the other components to travel down column (3). This cycle can be repeated as required by the rate of injection of the samples to be separated. It will be appreciated that if the mixture to be separated contains a number of components which can be separated by CE and each of which is required to be isolated in pure form then it will be necessary to increase the number of outlet arms accordingly, each with its own freeze thaw switching means.

It will be appreciated that alternative detector systems (6) may be used in place of the ultra violet detector system. The choice of the particular detector means is determined by the characteristics of the products to be separated.

The freeze thaw switching procedure according to the invention is particularly advantageous when used with electrically driven systems such as for example capillary electrophoresis and/or electrochromatography. The freezing of liquid produces an insulating segment in the capillary and this results in an instantaneous loss of current, halting electroendosmotic flow and electrophoretic processes. On thawing current is restored without the delays that normally arise from instrumental capacitance and thus precise knowledge of the location of analyte components can thereby be maintained.

An example of capillary tube connecting means for use with micro-analytical process according to the invention is illustrated in FIG. 2.

The capillary tubes (1,2,3) are fixed in a lower body member (8) which has a flat burnished or polished upper surface (9). The upper ends (10) of the capillary tubes are polished and flush with the upper surface (9). The upper body member (11) has a flat surface (12) into which are cut or fashioned micro-channels (13). The position of the micro-channels are such that they link up with the internal bores of the capillaries (14). The micro-channels (13) may be cut into the flat surfaces (12) by means of controlled laser beam cutting. Alternatively they may be made by photolithography.

The illustration in FIG. 2 shows a means according to the invention for connecting three capillary tubes all of which are directly connected to each other by separate micro-channels. It will be appreciated however that the connecting means according to the invention may also be used to connect just two capillary tubes or more than three capillary tubes. Further it will be understood that when it is desired to connect more than two capillary tubes it will not be necessary to provide linking micro-channels to connect each capillary tube with every other capillary tube unless this is desired.

In use the flow of liquid from one capillary tube to another via the appropriate micro channel is directed by stopping the liquid flow in one or more of the other capillary tubes. The switch of the liquid flow to another capillary tube may be achieved by stopping the flow in the first receiving capillary tube and allowing flow in the second receiving capillary tube.

The control of liquid flow in the capillary tubes may be achieved by the use of the freeze-thaw switching technique according to the invention. The liquid flow is stopped by freezing a small segment of the liquid in the capillary tube (1,2,3) or the connecting micro-channel (13). The flow may then be restored by the thawing of the frozen segment.

Preferably the means for rapidly freezing the liquid phase is a jet of cold gas directed onto the required segment of the capillary or tube or micro-channel. Conveniently the cooling gas is provided from a liquefied source of the gas under pressure such as liquid carbon dioxide or liquid nitrogen.

An alternative means for freezing the liquid phase in micro-channels is illustrated in FIG. 3. In the arrangement illustrated the micro-channels (21,22,23) are formed on the surface of a micro chip (20) which might form part of an upper body member as illustrated in FIG. 2. Alternatively the micro chip might be a "stand alone" device where connection to capillary tubes is unnecessary. In the arrangement of FIG. 3 the micro-channels are in a T configuration. Peltier cooling elements (24) are arranged next to each micro channel dose to their point of intersection.

The material to be separated flows, for example, through inlet micro-channel (21). If the component to be separated is required to go into micro channel (22) the Peltier cooling element (24) next to micro-channel (23) will be activated to stop the liquid flow in micro-channel (23). Once the required material has passed into micro channel (22) the Peltier cooling element (24) next to micro channel (22) is activated so as to stop the flow into micro-channel (22). At the same time the frozen fluid in micro channel (23) will be thawed to allow the other components to travel down micro-channel (23). In this arrangement micro-channel (21) is described as the liquid inlet. However it will be appreciated that any one or two of the micro-channels (21,22,23) could act as fluid inlets with the remaining micro channel(s) acting as an outlet(s) depending on the requirements of the particular application.

What is claimed is:

1. A method for managing liquid flow through tubing or channels of internal diameter between 2 $\mu$m and 1000 $\mu$m, without the use of mechanical values, by freezing the liquid and subsequently thawing the frozen liquid in a small segment of the tube or channel wherein the liquid is frozen by means of a jet of cold gas provided from a liquefied source of the gas under pressure which is directed onto the required segment of the tube or channel.

2. A method according to claim 1, wherein the gas source is liquid carbon dioxide.

3. A method according to claim 2, wherein the frozen liquid is thawed by means of a jet of warm gas.

4. A method according to claim 1, wherein the gas source is liquid nitrogen.

5. A method according to claim 4, wherein the frozen liquid is thawed by means of a jet of warm gas.

6. A method according to claim 1, wherein the frozen liquid is thawed by means of a jet of warm gas.

7. A method according to claim 6, wherein the warm gas is air.

* * * * *